(12) United States Patent
Bartlett

(10) Patent No.: US 10,966,654 B2
(45) Date of Patent: Apr. 6, 2021

(54) INTRA VAGINAL DEVICE TO AID IN TRAINING AND DETERMINING MUSCLE STRENGTH

(71) Applicant: Analytica Limited, Brisbane (AU)

(72) Inventor: Peter Bartlett, Brisbane (AU)

(73) Assignee: Analytica Limited, Brisbane (AU)

( * ) Notice: Subject to any disclaimer, the term of this patent is extended or adjusted under 35 U.S.C. 154(b) by 0 days.

(21) Appl. No.: 15/533,359

(22) PCT Filed: Oct. 16, 2015

(86) PCT No.: PCT/AU2015/000619
§ 371 (c)(1),
(2) Date: Jun. 5, 2017

(87) PCT Pub. No.: WO2016/119002
PCT Pub. Date: Aug. 4, 2016

(65) Prior Publication Data
US 2017/0332959 A1    Nov. 23, 2017

(30) Foreign Application Priority Data

Jan. 29, 2015   (AU) .............................. 2015900255

(51) Int. Cl.
*A61B 5/103* (2006.01)
*A61B 5/00* (2006.01)
(Continued)

(52) U.S. Cl.
CPC .......... *A61B 5/4337* (2013.01); *A61B 5/1107* (2013.01); *A61B 5/1121* (2013.01);
(Continued)

(58) Field of Classification Search
CPC ..... A61B 5/4337; A61B 5/6846; A61B 5/227; A61B 5/1121; A61B 5/1107;
(Continued)

(56) References Cited

U.S. PATENT DOCUMENTS

2009/0171144 A1   7/2009  Squicciarini
2010/0174218 A1   7/2010  Shim
(Continued)

FOREIGN PATENT DOCUMENTS

AU        739990 B2    6/1999
AU        780359 B2    6/2001
(Continued)

OTHER PUBLICATIONS

International Search Report dated Nov. 6, 2015 from corresponding International Application No. PCT/AU2015/000619 (four pages).

*Primary Examiner* — Navin Natnithithadha
*Assistant Examiner* — Andrey Shostak
(74) *Attorney, Agent, or Firm* — Kilpatrick Townsend & Stockton LLP

(57) ABSTRACT

A device (10) to be inserted in a woman's vagina to aid in measuring muscles operatively associated with the woman's vagina. The device (10) includes a motion detector (24) that is a gyroscope and that detects angular movement about at
(Continued)

least one axis, and preferably detects angular movement about three mutually perpendicular axes. Preferably the motion detector (24) is a combination of a gyroscope and accelerometer.

8 Claims, 3 Drawing Sheets

(51) Int. Cl.
*A61B 5/11* (2006.01)
*A61H 19/00* (2006.01)
*A61B 5/22* (2006.01)

(52) U.S. Cl.
CPC ............ *A61B 5/227* (2013.01); *A61B 5/6846* (2013.01); *A61H 19/44* (2013.01); *A61B 2562/0219* (2013.01); *A61B 2562/04* (2013.01); *A61H 2201/5061* (2013.01); *A61H 2201/5069* (2013.01); *A61H 2201/5084* (2013.01); *A61H 2201/5097* (2013.01)

(58) Field of Classification Search
CPC ........ A61B 2562/0219; A61B 2562/04; A61H 19/44; A61H 2201/5061; A61H 2201/5069; A61H 2201/5097; A61H 2201/5084

See application file for complete search history.

(56) References Cited

U.S. PATENT DOCUMENTS

| | | | |
|---|---|---|---|
| 2011/0196263 A1 | 8/2011 | Egorov et al. | |
| 2014/0066813 A1* | 3/2014 | Daly | A63B 23/20 600/591 |
| 2015/0032030 A1* | 1/2015 | Iglesias | A61B 5/103 600/587 |

FOREIGN PATENT DOCUMENTS

| | | | | |
|---|---|---|---|---|
| GB | 2492754 A | 1/2013 | | |
| WO | 92/20283 A1 | 11/1992 | | |
| WO | 2012/138232 A1 | 10/2012 | | |
| WO | 2012/142646 A1 | 10/2012 | | |
| WO | WO-2012142646 A1 * | 10/2012 | ............ | A63B 23/20 |
| WO | 2013/116310 A1 | 8/2013 | | |
| WO | 2015/103629 A1 | 7/2015 | | |
| WO | 2016/042310 A1 | 3/2016 | | |
| WO | 2016/067023 A1 | 5/2016 | | |

* cited by examiner

INTRA VAGINAL DEVICE TO AID IN TRAINING AND DETERMINING MUSCLE STRENGTH

This application is a U.S. National Phase Application of PCT/AU2015/000619, filed Oct. 16, 2015, which claims priority to Australian Provisional Application No. 2015900255, filed Jan. 29, 2015, the entireties of which are incorporated by reference herein.

FIELD

The present invention relates to intra vaginal devices to aid in determining muscle strength and more particularly but not exclusively to perineometers.

BACKGROUND

A perineometer is a medical instrument which measures the strength of voluntary contractions of pelvic floor muscles. It is widely believed that pelvic floor muscle strengthening leads to a lower likelihood of suffering from urinary incontinence. Typically a kegel exercise is used to improve strength. Several types of perineometers exist, most devices use vaginal pressure in order to provide a correlation to pelvic floor muscle strength.

The group of muscles involved in performing a kegel exercise (and hence responsible for continence) is the levator ani. Making up part of the levator ani is the pubococcygeus and the puborectalis. The pubococcygeus arises from pubis (pubic bone) and inserts into the lateral part of the coccyx (sides of coccyx) and so when contracted, presses bilaterally against the walls of the vagina. The puborectalis arises from the superior and inferior pubic rami (front part of pelvis, either side of pubis) and forms a sling around the rectum. Hence when contracted, it "pulls forward" to aid in closing off the canals. The strength of both is essential in maintaining continence.

Many perineometers currently available measure the pressure change inside the vaginal canal upon muscle contract. These devices have the disadvantage that they do not give any indication of muscle movement or actual contraction force. This may lead to deterioration of a patient's condition of if the patient is performing the contraction incorrectly the problem being that "bearing down" using the stomach muscles can also increase the pressure inside the vaginal canal, thus giving an incorrect indication of muscle contraction.

Known perineometers are described in Australian Patent 739990, Australian Patent 780359, International Patent Publication WO 92/20283, International Patent Publication WO 2012/142646 and USA Patent Application 2010/174218.

The device of WO 2012/142646 differs from other types of devices through the use of a superior direct muscle force measurement and positioning of the device in the vagina.

The above discussed devices have the disadvantage that they still fail to provide sufficiently accurate information in respect of contraction of the pelvic floor muscle group.

OBJECT OF THE INVENTION

It is the object of the present invention to overcome or substantially ameliorate the above disadvantage.

SUMMARY OF THE INVENTION

There is disclosed herein an intra vaginal device to aid in determining muscle contraction, the device including:
a body to be at least partly inserted into a vagina;
a motion detector mounted in the body to detect movement of the body resulting from muscular contraction adjacent the vagina and to generate a signal indicative of the movement; and
a circuit connected to the detector so as to receive the signals therefrom.

Preferably, the motion detector detects acceleration in at least one linear direction.

Preferably, the motion detector detects acceleration in three mutually perpendicular directions.

Preferably, the motion detector detects angular movement about at least one axis.

Preferably, the motion detector detects angular movement about three mutually perpendicular axes.

Preferably, the motion detector includes a gyroscope.

Preferably, the motion detector includes an accelerometer.

Preferably, the body is elongated so as to have an end portion, a base spaced from the end portion, and a longitudinally extending side wall extending between the end portion and the base;
and wherein the device further includes:
a first sensor, the sensor being mounted on the side wall and to provide an indication of pressure applied thereto; and
a second sensor, the second sensor being mounted on the side wall so as to be spaced angularly about said axis from the second sensor, and to provide an indication of the pressure applied to the second sensor.

Preferably, said end portion is convex.

Preferably, said side wall includes a first side wall portion to which the first sensor is attached, and a second side wall portion to which the second sensor is attached, with the second sensor being angularly displaced about said axis from the first sensor by approximately 80° to 90°.

Preferably, said side wall includes a third side wall portion, and the device further includes a third sensor attached to the third side wall portion, with the third sensor being spaced angularly about said axis from the first and second sensors.

Preferably, the third sensor is spaced approximately 80° to 90° from the first sensor.

Preferably, the wall portions are generally planar.

In an alternative preferred form, the wall portions are convex.

Preferably, at least one of the sensors provides an electrical resistance that diminishes with an increase of pressure applied thereto.

Preferably, the sensors are elongated longitudinally of said body.

Preferably, said base is elongated in a direction transverse of said direction.

Preferably, said base is adapted to engage the vaginal entrance to aid in correctly locating the sensors.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENT

Figure 1:
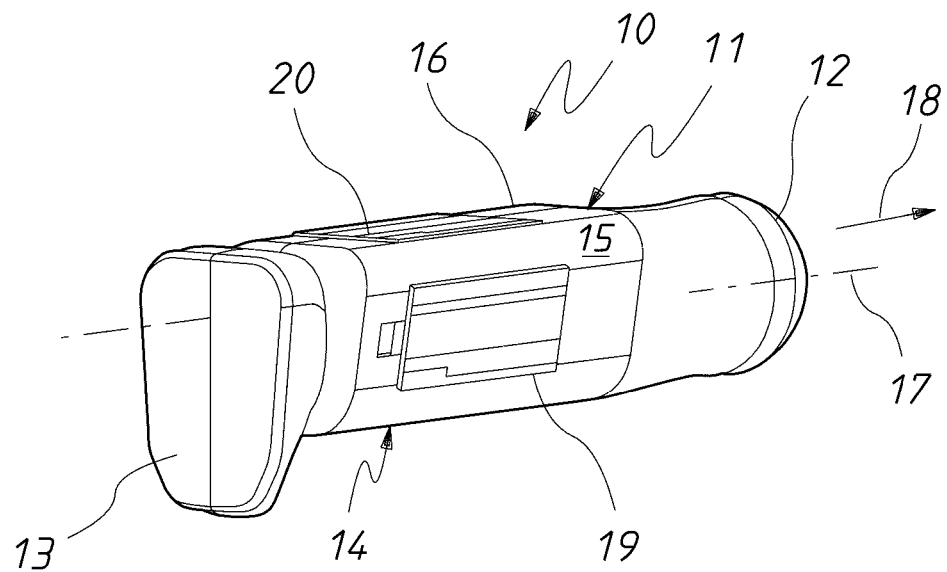
FIG. 1 is a schematic isometric view of a intra vaginal device to aid in measuring muscle strength.
Figures 2, 3:
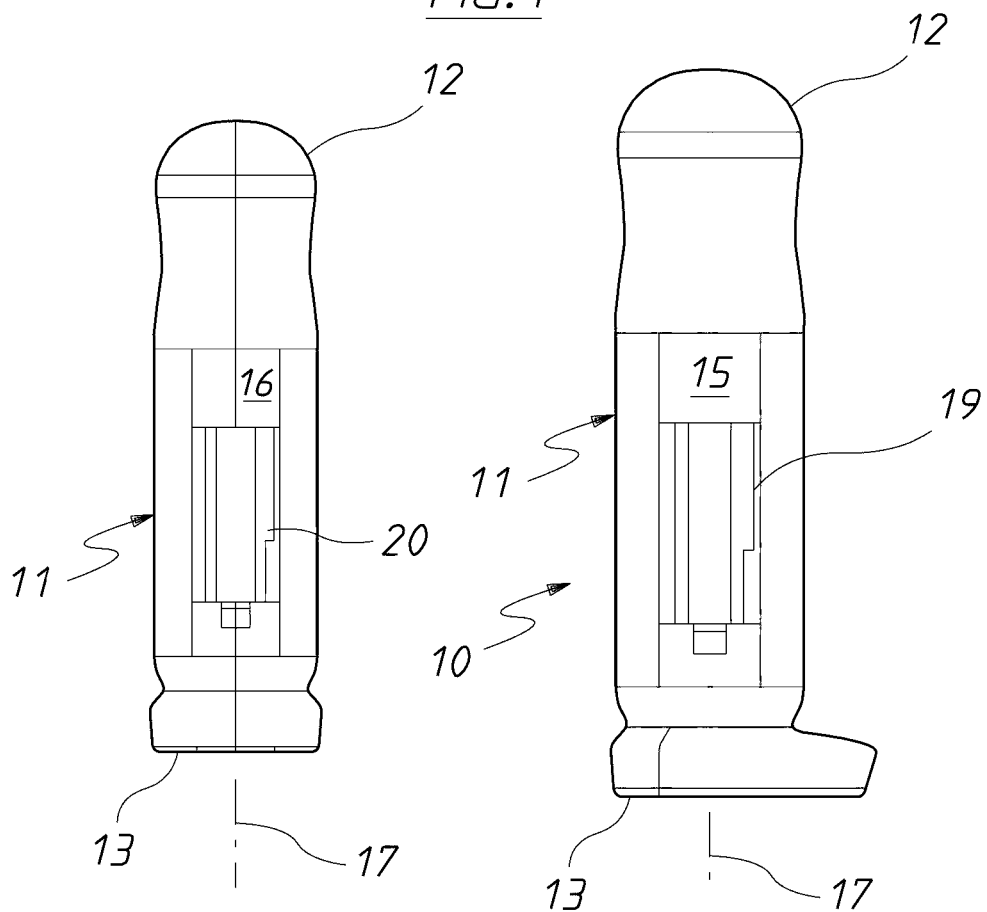
FIG. 2 is a schematic top plan view of the device of FIG. 1.
FIG. 3 is a schematic side elevation of the device of FIG. 1.
Figure 4:
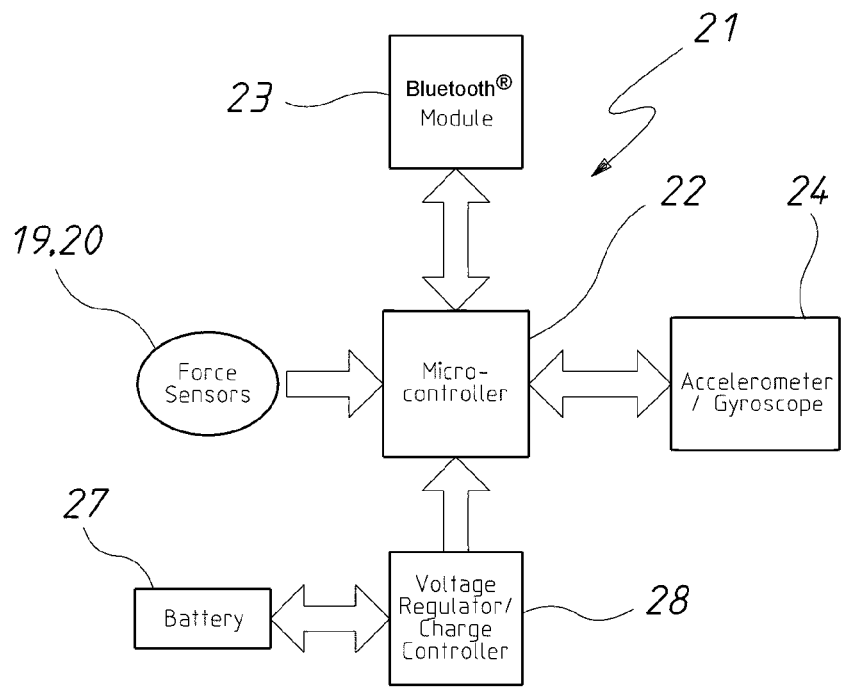
FIG. 4 is a schematic diagram of an electronic circuit employed in the device of FIG. 1.
Figure 5:
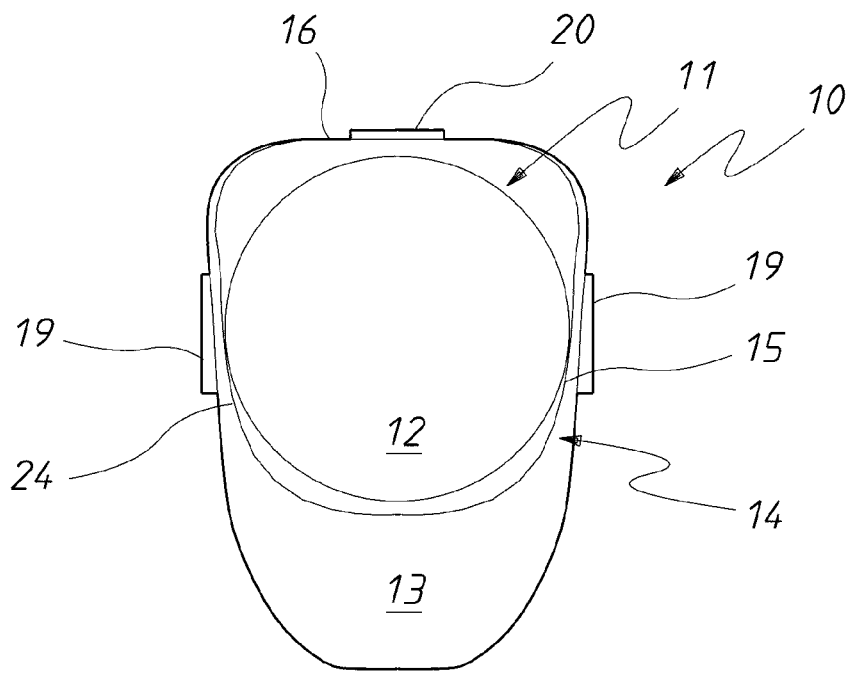
FIG. 5 is a schematic end elevation of the device of FIG. 1.
Figure 6:
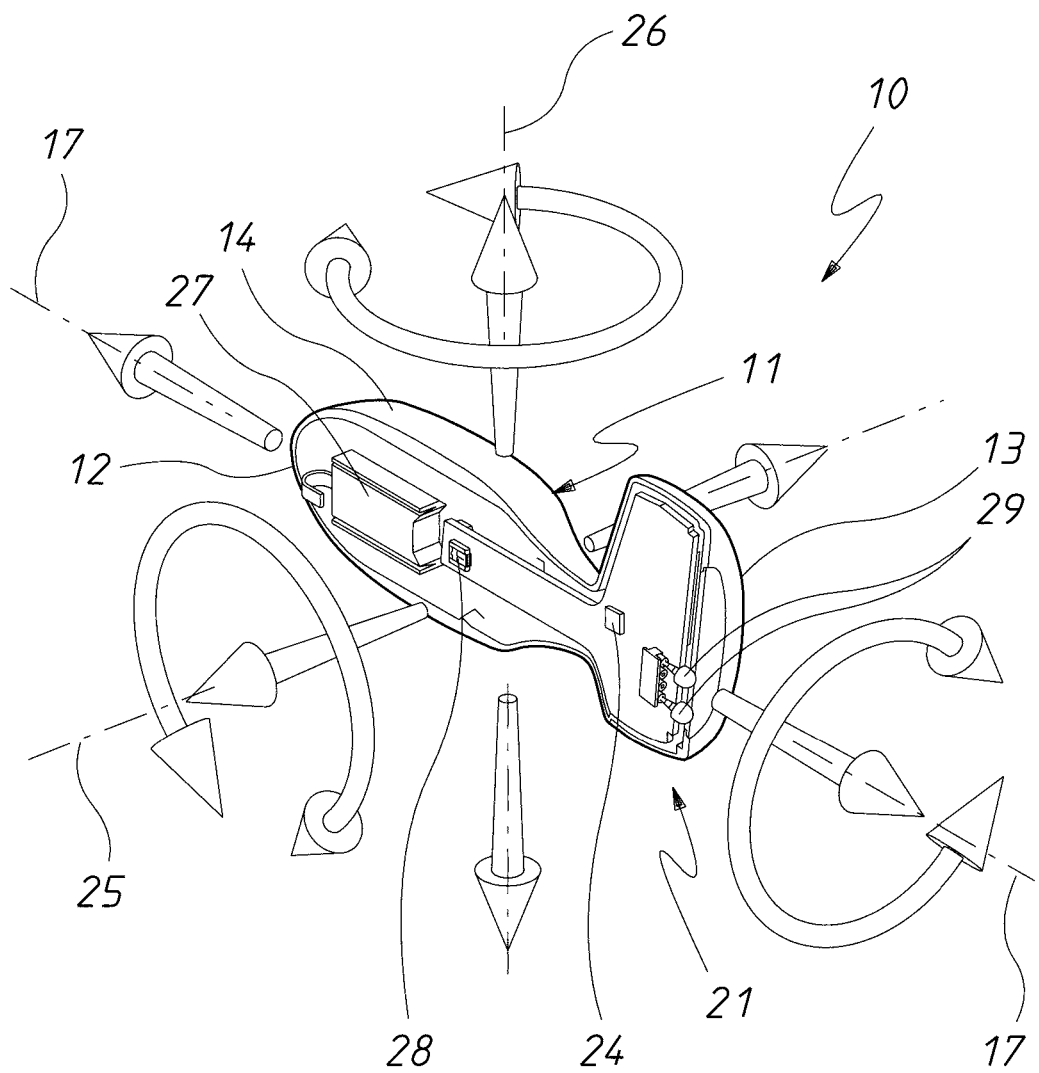
FIG. 6 is a schematic sectioned isometric view of the device of FIG. 1.

In the accompanying drawings there is schematically depicted a device 10 to be inserted in a woman's vagina to aid in measuring muscles operatively associated with the women's vagina.

The device 10 includes an elongated hollow body 11 having an end portion 12, a base 13 and a longitudinally extending side wall 14. The side wall 14 includes side wall portions 15, 16 and 24. Preferably, the side wall portions 15, 16 and 24 are generally planar (or convex) and the portion 12 generally convex.

The device 10 has a longitudinal axis 17.

Secured to each wall portion 15 and 24 is a sensor 19, while secured to the wall portion 16 is a sensor 20. Each of the sensors 19 and 20 is adapted to provide an indication of the pressure applied thereto. As a particular example, the sensors 19 and 20 could provide an electrical resistance that increases or decreases with pressure applied thereto, preferably decreases.

Preferably, the sensor 20 is spaced angularly about the axis 17 by an angle of approximately 80° to 90° from each of the sensors 19.

Preferably, the sensors 19 are spaced from the base 13 by the said distance. The sensor 20 is placed at a desired distance from the base 13, that may be the same or smaller distance from the base 13 than the sensors 19. Preferably, the sensors 19 and 20 are elongated longitudinally relative to the body 11.

Preferably, the base 13 is transversely elongated, relative to the axis 17, to aid a user to manipulate the device 10 and to aid in correctly positioning the device 10 by having the base 13 engage the vaginal entrance.

The sensor 20 provides an indication of the puborectalis contraction forces, the sensors 19 provide an indication of the pressure applied by the pubococcygeus.

The device 10 is shaped in such a way that once inserted into the vagina, it is able to measure both modes of contraction. The device 10 is inserted in the direction 18. The sensor 20 is preferably on top of the device 10 and measures the force applied to the device 10 by the urethral wall—thus capturing the contraction strength contributed by the puborectalis.

The sensors 19 are on the longitudinal sides of the device 10.

The base 13 is spaced from the sensors 19 and 20 so that the base 13 upon engaging the entrance of the vagina, correctly locates the sensors 19 and 20.

The sensors 19 are able to separately measure the force directly applied by the bilateral contraction of the pubococcygeus.

Preferably, the device 10 includes an electronic circuit 21 (printed circuit board) incorporating the sensors 19 and 20. The circuit 21 includes a processor 22 that interrogates the sensors 19 and 20 to determine their resistance, and then to provide a signal for a read out 23 that provides information in respect of the muscles associated with the user's vagina.

The read out 23 may be remote from body 11 and communicates via wireless (BLUETOOTH®) with the processor 22.

The circuit 21 also includes a motion detector 24. The motion detector 24 in one preferred form detects acceleration in at least one direction, and preferably detects acceleration in three mutually perpendicular linear directions. Again the detector is interrogated by the processor 22 that provides a signal to the read out 23.

In another preferred form, the motion detector 24 is a gyroscope that detects angular movement about at least one axis, and preferably detects angular movement about three mutually perpendicular axes. Most preferably the motion detector 24 is a combination of a gyroscope and accelerometer. One example of such a device is an Invesense MPU-6050 device that also has a standard 12C communications interface.

In one embodiment the motion detector 24 is a gyroscope that provides a signal indicative of angular movement about the mutually perpendicular axes 17, 25 and 26.

In an alternative embodiment, the motion detector 24 provides a signal indicative of acceleration in the directions of the three axes 17, 25 and 26.

In a further embodiment, the motion detector 24 provides signals indicative of angular movement about the axes 17, 25 and 26, as well as acceleration in linear directions along the axes 17, 25 and 26.

In respect of the above it should be appreciated that where the motion detector 24 provides a signal indicative of angular movement and acceleration, the axes about which the angular movement is measured, and the axes along which the acceleration takes place, need not be coincident. That is the axes about which the angular movement is measured may be displaced from the axes along which the acceleration is measured.

However, most preferably the axes are coincident.

Connected to the circuit 21 is a rechargeable battery 27, with the circuit 21 provided with a coupling 28 that may include a voltage regulator/charge controller. The coupling 28 provides for releasably attaching the battery 27 to the circuit 21. The circuit 21 is also provided with contacts 29 that provide for connection of the circuit 21 to a power supply for the purposes of recharging the battery 27.

Preferably the circuit 21 is constructed so that the motion detector 24 is located in or adjacent the base 13.

In operation of the above device 10, the force measurements provided by the sensors 19 and 20 can also be combined to give an average contraction strength output.

Separation of the measurements enables a more thorough understanding of the overall contraction and may lead to easier diagnosis of incontinence problems, as well as an invaluable teaching aide. There are many factors involved in incontinence, and this may enable clinicians to identify the muscle group that is contributing to incontinence in different case studies.

This specific feedback is also essential in encouraging and maintaining consistency with patients using the device.

The ability to distinguish between the specific muscles and modes of contraction may also be helpful in addressing a common issue of over-clenching of the pelvic floor. Many women suffer from this condition and need to be taught how to relax these muscles. The device 10 would be able to offer a more accurate picture of the clenching problem by measuring the full input of each muscle, and possibly pinpointing which area to focus on.

The motion detector 24 enables the device 10 to provide a more accurate determination in respect of whether the muscle movement correlates to correct exercise, as well as being able to detect a larger range of incorrect movement, that is movement in respect of lift and bearing down. The motion detector 24 also provides information in respect of offset angular movement.

Further to the above, the motion detector 24 also provides a better indication of whether contractions are correct.

The motion detector 24 also enables the device 10 to provide orientation detection such that the user's position during exercise can be recorded (standing or lying down, etc) in order to segregate the results.

Preferably in use of the device 10, the device 10 is covered by a sheath. As a particular example, the sheath may be of a synthetic rubber.

The invention claimed is:

1. An intra vaginal device to aid in determining muscle contraction, the device including:
 a body comprising:
 an end portion,
 a base spaced from the end portion in a direction along a longitudinal axis of the body, wherein the base is elongated in a direction transverse of the longitudinal axis, and
 a longitudinally extending side wall extending between the end portion and the base, wherein the side wall comprises a first side wall portion and a second side wall portion,
 wherein the body is configured to be inserted into a vagina of a patient with the end portion and side wall positioned within the vagina and the base outside of the vagina engaging a vaginal entrance of the vagina;
 a motion detector positioned within the base of the body and configured to detect acceleration and angular movement of the body resulting from muscular contraction adjacent the vagina and to generate a signal indicative of the acceleration and angular movement;
 a first sensor mounted on the first side wall portion and configured to provide a first signal indicative of pressure applied to the first sensor by puborectalis contractions of the patient, wherein the first sensor is elongated relative to the longitudinal axis of the body;
 a second sensor mounted on the second side wall portion, wherein the second sensor is angularly positioned about the longitudinal axis from the first sensor by approximately 80° to 90°, wherein the second sensor is configured to provide a second signal indicative of pressure applied to the second sensor by pubococcygeus contractions of the patient, and wherein the second sensor is elongated relative to the longitudinal axis of the body; and
 a circuit connected to the motion detector, the first sensor and the second sensor so as to receive the signals therefrom,
 wherein the motion detector comprises:
 an accelerometer configured to detect and provide a third signal to the circuit indicative of acceleration in three mutually perpendicular directions; and
 a gyroscope configured to detect and provide a fourth signal to the circuit indicative of angular movement about three mutually perpendicular axes, and
 wherein the first signal indicative of pressure applied to the first sensor, the second signal indicative of pressure applied to the second sensor, the third signal indicative of the acceleration detected by the motion detector, and the fourth signal indicative of the angular movement detected by the motion detector together provide an indication that the pressure applied to the first sensor and the pressure applied to the second sensor do not correlate to correct exercises associated with puborectalis contractions and pubococcygeus contractions.

2. The device of claim 1, wherein said end portion is convex.

3. The device of claim 1, wherein said side wall includes a third side wall portion, and the device further includes a third sensor attached to the third side wall portion, with the third sensor being spaced angularly about the longitudinal axis from the first and second sensors, and wherein the third sensor is configured to provide a fifth signal to the circuit indicative of pressure applied to the third sensor by the pubococcygeus contractions of the patient.

4. The device of claim 3, wherein the third sensor is angularly displaced about the longitudinal axis from the first sensor by approximately 80° to 90°.

5. The device of claim 3, wherein the first, second and third side wall portions are generally planar.

6. The device of claim 3, wherein the first, second and third side wall portions are convex.

7. The device of claim 1, wherein at least one of the first and second sensors provides an electrical resistance that diminishes with an increase of pressure applied thereto.

8. The device of claim 3, wherein the third sensor is elongated relative to the longitudinal axis of said body.

* * * * *